United States Patent
Kurasawa et al.

(10) Patent No.: US 11,625,603 B2
(45) Date of Patent: Apr. 11, 2023

(54) LEARNING-TYPE SIGNAL SEPARATION METHOD AND LEARNING-TYPE SIGNAL SEPARATION DEVICE

(71) Applicant: NIPPON TELEGRAPH AND TELEPHONE CORPORATION, Tokyo (JP)

(72) Inventors: Hisashi Kurasawa, Tokyo (JP); Takayuki Ogasawara, Atsugi (JP); Masumi Yamaguchi, Atsugi (JP); Shingo Tsukada, Atsugi (JP); Hiroshi Nakashima, Atsugi (JP); Takahiro Hata, Tokyo (JP); Nobuhiko Matsuura, Tokyo (JP)

(73) Assignee: NIPPON TELEGRAPH AND TELEPHONE CORPORATION, Tokyo (JP)

(*) Notice: Subject to any disclaimer, the term of this patent is extended or adjusted under 35 U.S.C. 154(b) by 544 days.

(21) Appl. No.: 16/607,357

(22) PCT Filed: Apr. 23, 2018

(86) PCT No.: PCT/JP2018/016472
§ 371 (c)(1),
(2) Date: Oct. 22, 2019

(87) PCT Pub. No.: WO2018/199031
PCT Pub. Date: Nov. 1, 2018

(65) Prior Publication Data
US 2020/0050937 A1    Feb. 13, 2020

(30) Foreign Application Priority Data

Apr. 27, 2017 (JP) .............................. JP2017-088717

(51) Int. Cl.
*G06N 3/08* (2006.01)
*G06N 3/04* (2006.01)
*G06N 3/063* (2006.01)

(52) U.S. Cl.
CPC ................. *G06N 3/08* (2013.01); *G06N 3/04* (2013.01); *G06N 3/063* (2013.01)

(58) Field of Classification Search
CPC ............ G06N 3/08; G06N 3/04; G06N 3/063; G06N 3/084; G06N 7/005; G06N 3/0454;
(Continued)

(56) References Cited

U.S. PATENT DOCUMENTS 8,699,971 B1 * 4/2014 Kadambe ............... H04B 17/27
455/500
2007/0165112 A1   7/2007 Shinmei et al.

FOREIGN PATENT DOCUMENTS

| JP | 2007189589 A | 7/2007 |
| JP | 2015031889 A | 2/2015 |
| WO | WO-2017/027856 A1 | 2/2017 |

OTHER PUBLICATIONS

Pascual, S., Bonafonte, A., & Serra, J. (2017). SEGAN: Speech enhancement generative adversarial network. arXiv preprint arXiv: 1703.09452. (Year: 2017).*

(Continued)

*Primary Examiner* — Brian M Smith
*Assistant Examiner* — Henry Trong Nguyen
(74) *Attorney, Agent, or Firm* — Harness, Dickey & Pierce, P.L.C.

(57) ABSTRACT

A learning-type signal separation method performed using a model formulation unit, which performs learning processing based on a training-use signal including a specific component, and a training-use signal not including the specific component, the training-use signals including a common (Continued)

characteristic. The learning-type signal separation method includes: generating learned data by causing the model formulation unit to perform learning processing based on the training-use signal and information indicating whether or not the specific component is included in the training-use signal, to generate a data series signal in which the specific component has been separated and removed from a data series of the training-use signal; acquiring an arbitrary signal including the common characteristic; and generating, based on the acquired arbitrary signal and the generated learned data, a data series signal in which the specific component has been separated and removed from a data series of the arbitrary signal.

6 Claims, 9 Drawing Sheets

(58) Field of Classification Search
CPC ..... A61B 5/349; A61B 5/4866; A61B 5/7267; A61B 5/7275
See application file for complete search history.

(56) References Cited

OTHER PUBLICATIONS

Kwak, H., & Zhang, B. T. (2016). Generating images part by part with composite generative adversarial networks. arXiv preprint arXiv:1607.05387. (Year: 2016).*

Basser, P. J., Pajevic, S., Pierpaoli, C., Duda, J., & Aldroubi, A. (2000). In vivo fiber fractography using DT-MRI data. Magnetic resonance in medicine, 44(4), 625-632. (Year: 2000).*

Galteri, Leonardo et al. "Deep Generative Adversarial Compression Artifact Removal", arxiv.org, Cornell University Library, 201 Olin Library Cornell University, Ithaca, NY 14853, Apr. 8, 2017, XP080761668, DOI:10.1109/ICCV.2017.517.

Takayuki Ogasawara, Kazuyoshi Ono, Nobuaki Matsuura, Masumi Yamaguchi, Junji Watanabe, and Shingo Tsukada, "Development of Applications for a Wearable Electrode Embedded in Inner Shirt", NTT Technical Journal, Nov. 2014, pp. 16-20.

Taigang He, Gari Clifford, and Lionel Tarassenko, "Application of independent component analysis in removing artefacts from the electrocardiogram", Neural Comput & Applic, (2006), pp. 105-116.

MA Mneimneh, EE Yaz, MT Johnson, RJ Povinelli, "An Adaptive Kalman Filter for Removing Baseline Wandering in ECG Signals", Computers in Cardiology 2006; 33:253-256.

Juan Pablo Martinez, et al., "A Wavelet-Based ECG Delineator: Evaluation on Standard Databases", IEEE Transactions On Biomedical Engineering, vol. 51, No. 4, Apr. 2004, pp. 570-581.

Xiong, Peng, et al., "ECG signal enhancement based on improved denoising auto-encoder", Engineering Applications of Artificial Intelligence, 52 (2016), pp. 194-202.

Ian J. Goodfellow et al., "Generative Adversarial Nets", Proceedings of Advances in Neural Information Processing Systems 27 (NIPS 2014), The Neural Information Processing Systems Foundation, Dec. 13, 2014, pp. 1-9.

International Search Report (in English and Japanese) issued in International Application No. PCT/JP2018/016472, dated Jul. 10, 2018; ISA/JP.

* cited by examiner

LEARNING-TYPE SIGNAL SEPARATION METHOD AND LEARNING-TYPE SIGNAL SEPARATION DEVICE

CROSS-REFERENCE TO RELATED APPLICATIONS

This application is a 371 U.S. National Phase of International Application No. PCT/JP2018/016472, filed on Apr. 23, 2018, which claims priority to Japanese Application No. 2017/088717, filed on Apr. 27, 2017. The entire disclosures of the above applications are incorporated herein by reference.

TECHNICAL FIELD

The present invention relates to a learning-type signal separation method and a learning-type signal separation device.

BACKGROUND ART

An electrocardiogram is a graphical representation of a biological signal that fluctuates due to various factors such as blood circulation state and mental tension. The analysis results of an electrocardiogram are applied to various uses such as; diagnosis of diseases such as arrhythmia, evaluation of autonomic nervous function, and health condition and physical condition management. The measurement of a biological signal used in an electrocardiogram is, for example, performed using a measurement unit having a biological electrode as presented in Non-Patent Document 1.

In order to measure a biological signal correctly, it is necessary to keep the measuring unit in close contact with the body. However, wearable-type measuring units experience signal distortions and noise due to body movements or vibration and floating of the sensor. Consequently, the inability to make accurate measurements or judgments is a problem. As techniques for separating unnecessary signals such as signal distortion or noise, techniques such as independent component analysis, state space models, and frequency conversion are known.

CITATION LIST

Non-Patent Document

Non-Patent Document 1: Takayuki Ogasawara, Kazuyoshi Ono, Nobuaki Matsuura, Masumi Yamaguchi, Junji Watanabe, Shingo Tsukada, "Application of Wearable Electrode Inner Technology", NTT Technical Journal, November 2014, pp. 16-20.
Non-Patent Document 2: Taigang He, Gari Clifford, and Lionel Tarassenko, "Application of independent component analysis in removing artefacts from the electrocardiogram", Neural Comput & Applic, (2006), pp. 105-116.
Non-Patent Document 3: M A Mneimneh, E E Yaz, M T Johnson, R J Povinelli, "An Adaptive Kalman Filter for Removing Baseline Wandering in ECG Signals", Computers in Cardiology 2006; 33:253-256.
Non-Patent Document 4: Juan Pablo Martinez, et al., "A Wavelet-Based ECO Delineator: Evaluation on Standard Databases", IEEE TRANSACTIONS ON BIOMEDICAL ENGINEERING, VOL. 51, NO. 4, APRIL 2004, pp. 570-581.
Non-Patent Document 5: Xiong, Peng, et al., "ECG signal enhancement based on improved denoising auto-encoder", Engineering Applications of Artificial Intelligence, 52 (2016), pp. 194-202.

SUMMARY OF THE INVENTION

Problems to be Solved by the Invention

Independent component analysis assumes that each component is independent in a multivariate signal composed of a plurality of additive components, and separates the components so as to reduce the amount of mutual information between the components (for example, see Non-Patent Document 2). Independent component analysis is applied, for example, to sound source separation, which extracts the voice of a specific person from audio of a conversation between multiple people. However, the technique is effective for data having multiple measured points, and therefore there is a problem that application is difficult to biological signal data that has been measured at a single point.

State space models assume that each component is independent in a multivariate signal composed of a plurality of additive components, and separate the components by expressing each component with an appropriate model such as a trend, autoregression, or seasonal variation model (for example, see Non-Patent Document 3). State space models are applied to analysis of store sales data observed in a time series. However, a biological signal used in an electrocardiogram is a signal in which various factors such as blood circulation state and degree of mental tension act in combination, and there is a problem that it is difficult to model such factors precisely.

Separation by frequency transformation assumes that the frequency characteristic of each component in a multivariate signal composed of a plurality of additive components is different, and separates the components by transforming the signal into a frequency domain representation by Fourier transformation or wavelet transformation (for example, see Non-Patent Documents 4 and 5). Separation by frequency conversion is applied when removing low-frequency noise and high-frequency noise. However, there is a problem that application is difficult if the frequency characteristic of a component having a characteristic to be separated is not obtained in advance.

In view of the above circumstances, the present invention has an object of providing a technique which, for a signal measured at a single point and a signal in which modeling of the signal components is difficult, is capable of separating and removing a specific component included in the signal, even when the characteristics of the specific component such as signal distortion or noise is unknown.

Means for Solving the Problems

An aspect of the present invention is a learning-type signal separation method performed using a model formulation unit, which performs learning processing based on a training-use signal including a specific component, and a training-use signal not including the specific component, the training-use signals including a common characteristic. The learning-type signal separation method includes: generating learned data by causing the model formulation unit to perform learning processing based on the training-use signal and information indicating whether or not the specific component is included in the training-use signal, to generate a data series signal in which the specific component has been separated and removed from a data series of the training-use signal; acquiring an arbitrary signal including the common characteristic; and generating, based on the acquired arbitrary signal and the generated learned data, a data series signal in which the specific component has been separated and removed from a data series of the arbitrary signal.

An aspect of the present invention is the learning-type signal separation method described above, wherein the model formulation unit is a GAN (Generative Adversarial Network) including a classification unit, a generator, and a learning processing unit that causes the classification unit and the generator to perform learning, the learning-type signal separation method further comprises: providing, by the learning processing unit, taking the training-use signal as an input signal, the input signal and information indicating whether or not the specific component is included in the input signal to the classification unit and the generator, causing the classification unit to perform learning such that the classification unit outputs a classification result indicating whether or not the specific component is included in the input signal; causing the generator to perform learning such that the generator generates a data series signal in which the specific component has been separated and removed from a data series of the input signal; and causing the classification unit to perform learning such that the specific component is included in the input signal, while causing the generator to perform learning so as to cause the classification unit to classify that the specific component is not included in the input signal, at the time an output signal of the generator is provided as the input signal of the classification unit; in the generating, based on signal separation model data and the acquired arbitrary signal, a data series signal in which the specific component has been separated and removed from a data series of the arbitrary signal are generated, the signal separation model data being learned data from the generator among the generated learned data.

An aspect of the present invention is the learning-type signal separation method described above, wherein processes by the learning processing unit further comprises: causing the classification unit to perform learning such that the classification unit outputs a classification result indicating that the specific component is included when the specific component is included in the input signal, and outputs a classification result indicating that the specific component is not included in the input signal when the specific component is not included in the input signal; causing the classification unit to perform learning such that the classification unit outputs a classification result indicating that the specific component is included in the input signal at the time an output signal output by the generator resulting from providing the input signal including the specific component to the generator is provided to the classification unit as the input signal; and causing the classification unit to perform learning such that the classification unit outputs a classification result indicating that the specific component is not included in the input signal at the time an output signal output by the generator resulting from providing the input signal including the specific component to the generator is provided to the classification unit as the input signal.

An aspect of the present invention is the learning-type signal separation method described above, wherein processes by the learning processing unit further comprises: causing the classification unit to perform learning such that the classification unit outputs a classification result indicating that the specific component or a component newly added by the generator is included in the input signal when the specific component is included in the input signal, and outputs a classification result indicating that the specific component and a component newly added by the generator is not included in the input signal when the specific component is not included in the input signal; causing the classification unit to perform learning such that the classification unit outputs a classification result indicating that the specific component or a component newly added by the generator is included in the input signal at the time an output signal output by the generator resulting from providing the input signal to the generator is provided to the classification unit as the input signal; and causing the classification unit to perform learning such that the classification unit outputs a classification result indicating that the specific component and a component newly added by the generator is not included at the time an output signal output by the generator resulting from providing the input signal to the generator is provided to the classification unit as the input signal.

An aspect of the present invention is the learning-type signal separation method described above, wherein processes by the learning processing unit further comprises causing the generator to perform learning such that the same data series signal as a data series of the input signal is generated when the specific component is not included in the input signal provided to the generator.

An aspect of the present invention is the learning-type signal separation method described above, wherein the training-use signal, the arbitrary signal, and the data series signal are multivariate signals constituted by a plurality of additive components, or a univariate signal.

An aspect of the present invention is the learning-type signal separation method described above, wherein the training-use signal, the arbitrary signal, and the data series signal are measured biological signals, and the specific component is an unnecessary component added to the biological signal. An aspect of the present invention is the learning-type signal separation method described above, wherein the data series is a waveform or a frequency.

An aspect of the present invention is a learning-type signal separation device including: a training signal acquisition unit configured to acquire and classifies a signal as a training-use signal including a specific component or a training-use signal not including the specific component, the training-use signals including a common characteristic; a model formulation unit configured to, based on the training-use signal acquired by the training signal acquisition unit and information indicating whether or not the specific component is included in the training-use signal, perform learning that generates a data series signal in which the specific component has been separated and removed from a data series of the training-use signal, and generate learned data; a test signal acquisition unit configured to acquire an arbitrary signal including the common characteristic; and a signal separation removal unit configured to, based on the arbitrary signal acquired by the test signal acquisition unit and the generated learned data, generate a data series signal in which the specific component has been separated and removed from a data series of the arbitrary signal.

Effects of the Invention

The present invention enables, for a signal measured at a single point and a signal in which modeling of the signal components is difficult, the separation and removal of a specific component included in the signal, even when the characteristics of a specific component such as signal distortion or noise is unknown.

EMBODIMENTS FOR CARRYING OUT THE INVENTION

Figure 1:
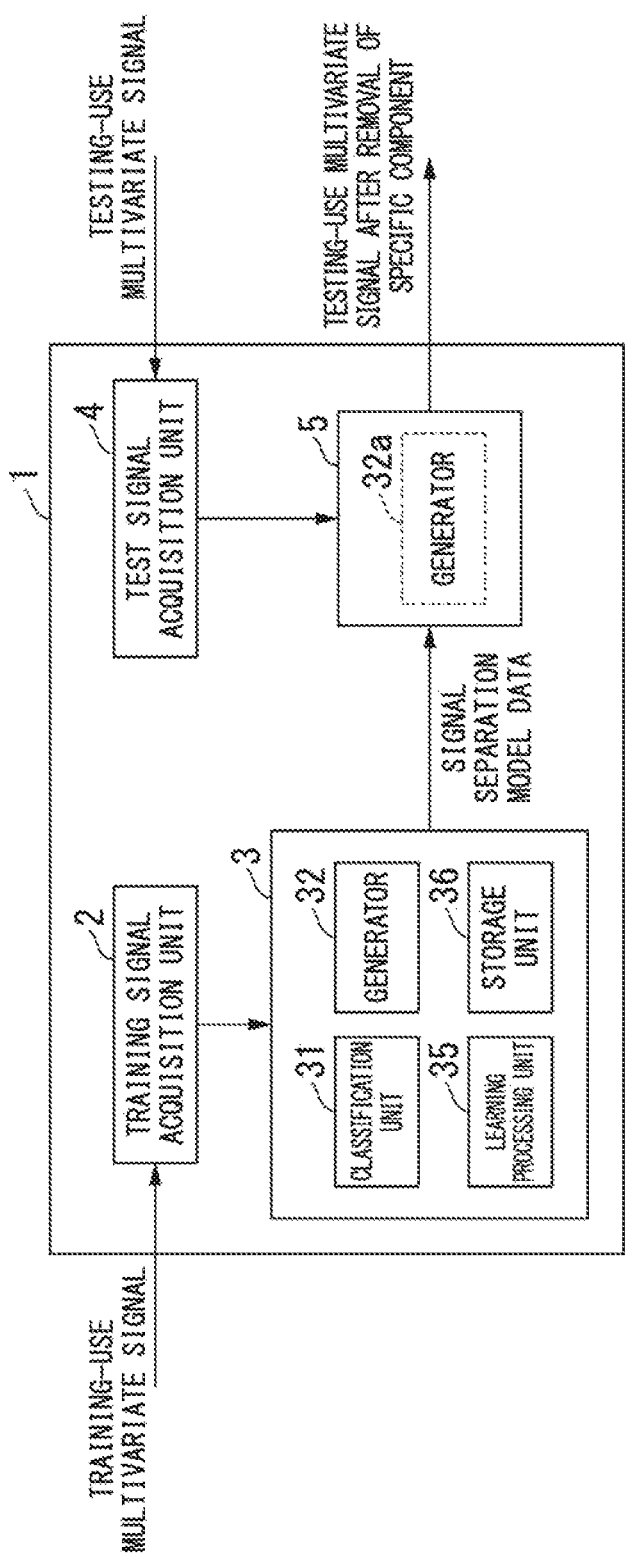
FIG. 1 is a block diagram showing a configuration of a learning-type signal separation device according to an exemplary embodiment of the present invention.
Figure 2:
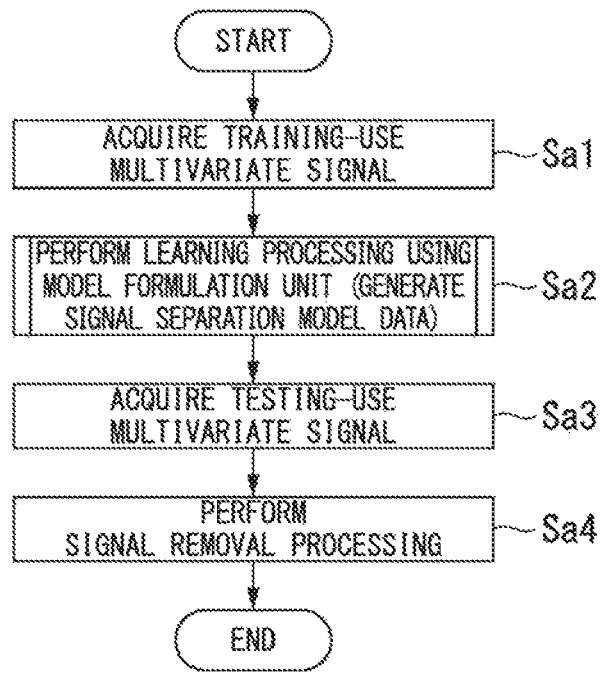
FIG. 2 is a flowchart showing the flow of a learning-type signal separation method performed by the learning-type signal separation device according to the same embodiment.

Hereunder, an embodiment of the present invention will be described with reference to the drawings. FIG. 1 is a block diagram showing a configuration of a learning-type signal separation device 1 according to an exemplary embodiment of the present invention. The learning-type signal separation device 1 includes; a training signal acquisition unit 2, a model formulation unit 3, a test signal acquisition unit 4, and a signal separation removal unit 5. The training signal acquisition unit 2 acquires an externally provided training-use multivariate signal. Here, a multivariate signal is composed of a plurality of additive components, and may be a time series signal having a single series or a time series signal having multiple series measured at the same time. Furthermore, although the multivariate signal is difficult to model because various factors are acting in combination, it is, for example, a signal that includes a common characteristic.

The multivariate signal is, for example, a biological signal, or a sound or image signal. The present embodiment exemplifies a case where the multivariate signal is a biological signal. A biological signal is a signal obtained by measuring the state of a living body, and is a signal described by a quantitative value. When the multivariate signal is a biological signal, the multivariate signal includes a common characteristic such as a P, Q, R, S, and T wave which repeatedly appears in a biological signal used in an electrocardiogram.

An externally provided training-use multivariate signal may be a multivariate signal including a specific component or a multivariate signal not including the specific component. The training signal acquisition unit 2 acquires the signal and classifies whether or not the specific component is included in the acquired multivariate signal. The specific component is, for example, an unnecessary component such as signal distortion or noise which depends on the performance of the measurement unit and is originally present in the measured signal, or noise and the like which becomes mixed at the time of the measurement.

The specific component is not limited to an independent component such as signal distortion or noise. For example, in the case where the biological signal is a cardiac potential, the signal may be treated as multivariate signals including the specific component for separating moving averages and moving averages having an abnormal value. Furthermore, in the case where the moving average of the cardiac potential over one second falls below −600 μV or exceeds 600 μV, the signal may be treated as a multivariate signal including the specific component to be separated, assuming that the signal includes signal distortion or noise with a high probability. Moreover, in the case where the moving standard deviation of the cardiac potential over one second exceeds 600 μV or falls below 40 μV, the signal may similarly be treated as a multivariate signal including the specific component to be separated, assuming that the signal includes signal distortion or noise with a high probability.

The model formulation unit 3 performs learning based on the training-use multivariate signal acquired by the training signal acquisition unit 2, and generates signal separation model data that separates a specific component from the multivariate signal. The model formulation unit 3 includes; a classification unit 31, a generator 32, a learning processing unit 35, and a storage unit 36, which constitute a GAN (Generative Adversarial Network). When the classification unit 31 takes a multivariate signal as an input signal after sufficient learning has been performed, it classifies whether or not the signal includes the specific component to be separated and outputs a classification result. When the generator 32 takes a multivariate signal as an input signal after sufficient learning has been performed, it generates a data series signal in which the specific component to be separated has been separated and removed from the multivariate signal data series. The multivariate data series is, for example, a waveform of the multivariate signal or the frequency of the multivariate signal. In the present embodiment, processing that generates a signal having a waveform obtained by separating and removing the specific component to be separated from the waveform of a multivariate signal is exemplified.

The classification unit 31 and the generator 32 respectively correspond to a discriminator and a generator of the GAN. A functional unit that performs learning in the discriminator and the generator corresponds to the learning processing unit 35. The classification unit 31 and the generator 32 are each, for example, a multi-layer perceptron, and learning is performed by an internal weight coefficient being changed by the learning processing unit 35.

The learning processing unit 35 provides a training-use multivariate signal not including the specific component as the input signal, to the classification unit 31, and learning is performed by changing the internal weight coefficient of the classification unit 31 such that the classification unit 31 outputs that "the specific component and a component newly added by the generator 32 is not included". Furthermore, the learning processing unit 35 provides a training-use multivariate signal including the specific component, to the classification unit 31 as the input signal, and learning is performed by changing the internal weight coefficient of the classification unit 31 such that the classification unit 31 outputs that "the specific component or a component newly added by the generator 32 is included".

Here, the component newly added by the generator 32 is an additional component that the generator 32 adds to an output signal which is generated and output by the generator 32 based on an input signal. For example, the component newly added by the generator 32 is a difference component between the output signal of the generator 32 when a training-use multivariate signal not including the specific component is provided as the input signal of the generator 32, and the input signal. Furthermore, the component newly added by the generator 32 is also a difference between a signal obtained by adding the specific component to the output signal of the generator 32 when a training-use multivariate signal including the specific component is provided as the input signal of the generator 32, and the input signal. As a result, the component newly added by the generator 32 is reduced as learning proceeds.

Furthermore, the learning processing unit 35 provides to the classification unit 31 the output signal which is output by the generator 32 as a result of providing a training-use multivariate signal to the generator 32, and learning is performed by changing the internal weight coefficient of the classification unit 31 such that the classification unit 31 outputs that "the specific component or a component newly added by the generator 32 is included".

Furthermore, the learning processing unit 35 provides a training-use multivariate signal not including the specific component, to the generator 32, and learning is performed by changing the internal weight coefficient of the generator 32 such that the generator 32 generates and outputs a signal having the same waveform as the input signal. Furthermore, when the learning processing unit 35 provides to the generator 31 the output signal which is output by the generator 32 as a result of providing a training-use multivariate signal to the generator 32, learning is performed by changing the internal weight coefficient of the generator 32 such that the classification unit 31 outputs that "the specific component and a component newly added by the generator 32 is not included". The storage unit 36 stores the latest weight coefficients of the classification unit 31 and the generator 32, which are updated in the learning process performed by the learning processing unit 35.

The test signal acquisition unit 4 acquires an externally supplied testing-use multivariate signal. The testing-use multivariate signal is an arbitrary signal in which it is not known whether the signal includes the specific component. For example, in practice, a biological signal such as a cardiac potential measured from an arbitrary subject is applied. The signal separation removal unit 5 reads information relating to the weight coefficient of the generator 32 stored in the storage unit 36 of the model formulation unit 3, as signal separation model data. Furthermore, the signal separation removal unit 5 internally generates a generator 32a having the same configuration as the generator 32 based on the read signal separation model data. Moreover, the signal separation removal unit 5 provides a testing-use multivariate signal to the generator 32a as an input signal. The generator 32a outputs a signal generated by separating and removing the specific component from the input signal.

(Processing of Learning-Type Signal Separation Device)

Next, the flow of processing of a learning-type signal separation method performed by the learning-type signal separation device 1 will be described with reference to FIG. 2 to FIG. 7. The training signal acquisition unit 2 takes an externally supplied training-use multivariate signal as an input signal. At this time, the training signal acquisition unit 2 takes the signal and determines whether or not the specific component is included in the training-use multivariate signal (step Sa1). The model formulation unit 3 starts a learning processing subroutine that generates signal separation model data (step Sa2).

Figure 3:
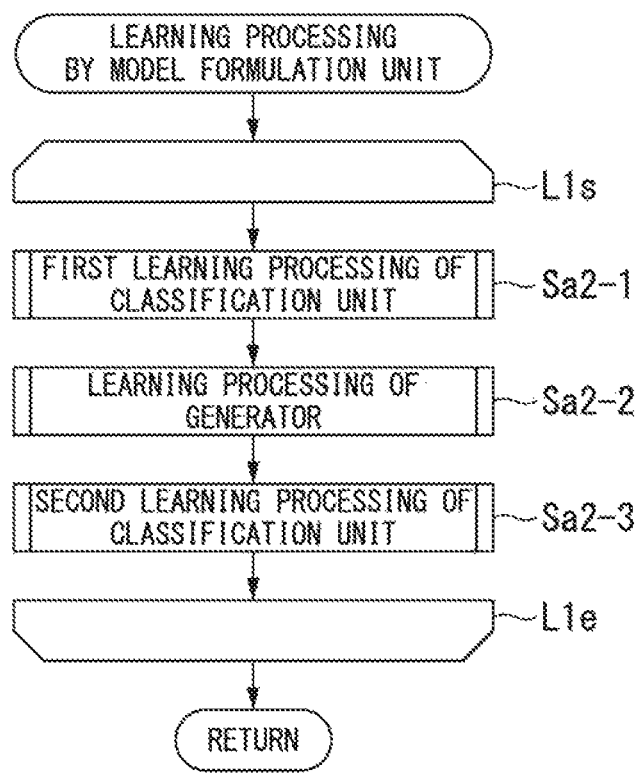
FIG. 3 is a flowchart showing the flow of learning processing by a model formulation unit according to the same embodiment.

Proceeding to FIG. 3, in the model formulation unit 3, a first learning processing of the classification unit 31 which causes the classification unit 31 to perform learning using the training-use multivariate signal is performed by the learning processing unit 35 (step Sa2-1). After the first learning processing of the classification unit 31, learning processing of the generator 32 which causes the generator 32 to perform learning using the training-use multivariate signal is performed by the learning processing unit 35 (step Sa2-2). After the learning processing of the generator 32, a second learning processing of the classification unit 31 which causes the classification unit 31 to perform learning using an output signal from the generator 32 is performed by the learning processing unit 35 (step Sa2-3). The processing of steps Sa2-1, Sa2-2, and Sa2-3 is repeatedly performed a predetermined number of times (loop L1s to L1e). Here, the predetermined number of times is, for example, the number of times that sufficient learning is assumed to be performed.

Figure 4:
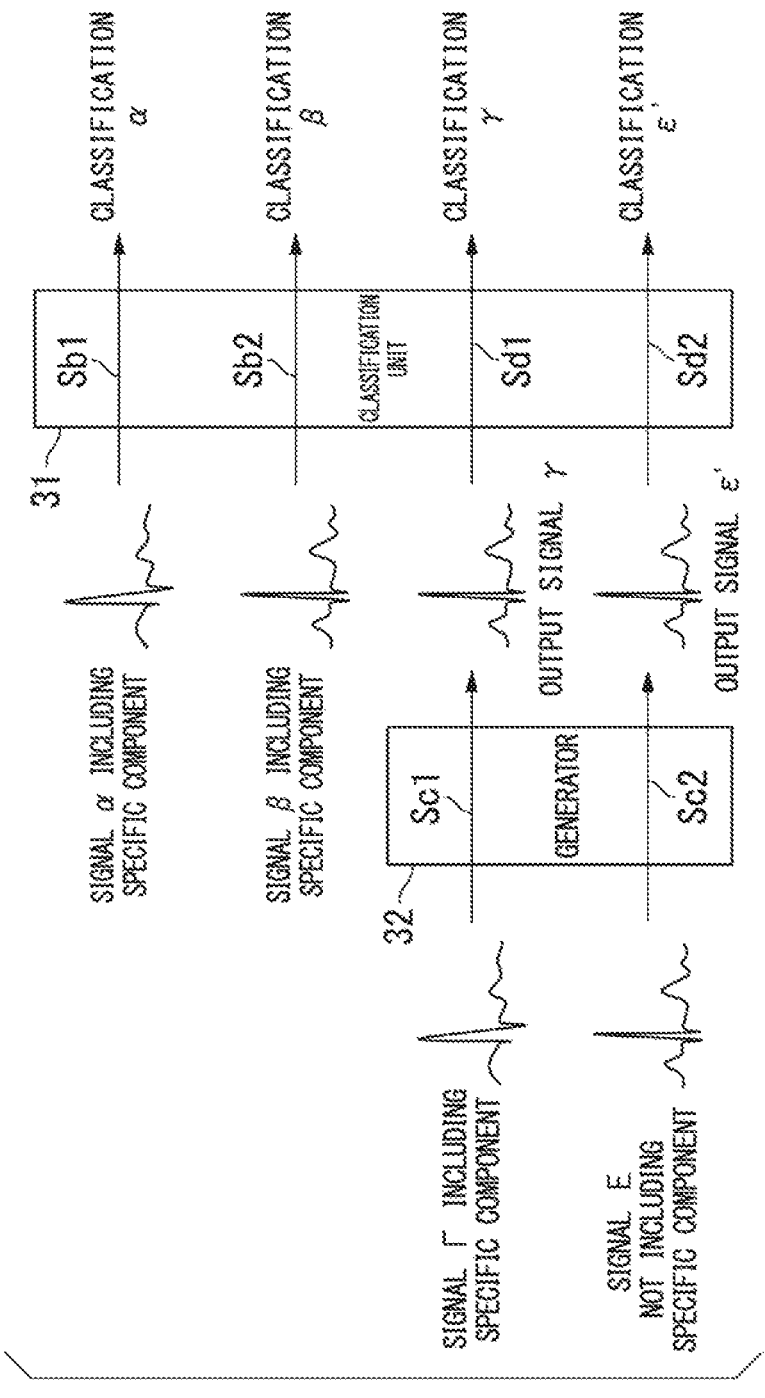
FIG. 4 is a diagram describing the flow of learning processing by the model formulation unit according to the same embodiment.

FIG. 4 is a diagram conceptually showing the processing of steps Sa2-1, Sa2-2, and Sa2-3 performed by the learning processing unit 35. The first learning processing of the classification unit 31 in step Sa2-1 corresponds to steps Sb1 and Sb2 in FIG. 4. The learning processing of the generator 32 in step Sa2-2 corresponds to steps Sc1 and Sc2 in FIG. 4. The second learning processing of the classification unit 31 in step Sa2-3 corresponds to steps Sd1 and Sd2 in FIG. 4. The details of the respective processing will be described with reference to FIG. 4 to FIG. 7.

Figure 5:
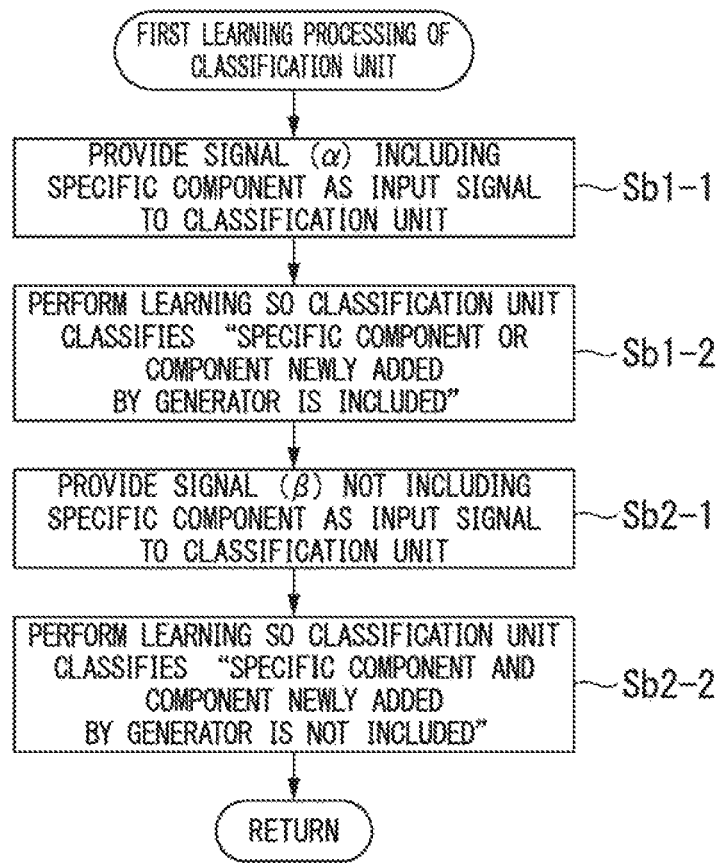
FIG. 5 is a flowchart showing the flow of first learning processing by a classification unit according to the same embodiment.

FIG. 5 is a flowchart showing the flow of the first learning processing of the classification unit 31 in step Sa2-1. The learning processing unit 35 provides a training-use multivariate signal ($\alpha$) including the specific component to the classification unit 31 as an input signal (step Sb1-1). The classification unit 31 calculates an output value based on the internal weight coefficient and the input signal ($\alpha$), and outputs a classification $\alpha$ as the classification result. The learning processing unit 35, based on the information indicated by the classification $\alpha$, causes the classification unit 31 to perform learning such that the information indicated by the classification $\alpha$ becomes information that indicates that "the specific component or a component newly added by the generator 32 is included" (step Sb1-2).

For example, the classification result output by the classification unit 31 is a probability value represented by a value between 0 and 1 which is predefined such that information indicating that "the specific component or a component newly added by the generator 32 is included" is represented by "1", and information indicating that "the specific component and a component newly added by the generator 32 is not included" is represented by "0".

At this time, the learning processing unit 35 calculates an internal weight coefficient of the classification unit 31 using a predetermined error function so that the value of the classification $\alpha$ approaches "1", and rewrites and updates the internal weight coefficient of the classification unit 31 with the calculated weight coefficient. The learning processing unit 35 writes and stores the calculated weight coefficient of the classification unit 31 in the storage unit 36.

The learning processing unit 35 provides a training-use multivariate signal ($\beta$) not including the specific component to the classification unit 31 as an input signal (step Sb2-1). The classification unit 31 calculates an output value based on the internal weight coefficient and the input signal ($\beta$), and outputs a classification $\beta$ as the classification result. The learning processing unit 35, based on the information indicated by the classification β, causes the classification unit 31 to perform learning such that the information indicated by the classification β becomes information that indicates that "the specific component and a component newly added by the generator 32 is not included" (step Sb2-2).

That is to say, the learning processing unit 35 calculates an internal weight coefficient of the classification unit 31 so that the value of the classification 1 approaches "0", and rewrites and updates the internal weight coefficient of the classification unit 31 with the calculated weight coefficient. The learning processing unit 35 writes and stores the calculated weight coefficient of the classification unit 31 in the storage unit 36.

The first learning processing of the classification unit 31 shown in FIG. 5 represents supervised learning, which has information indicating "the specific component or a component newly added by the generator 32 is included", and information indicating "the specific component and the component newly added by the generator 32 is not included" as teaching data.

Figure 6:
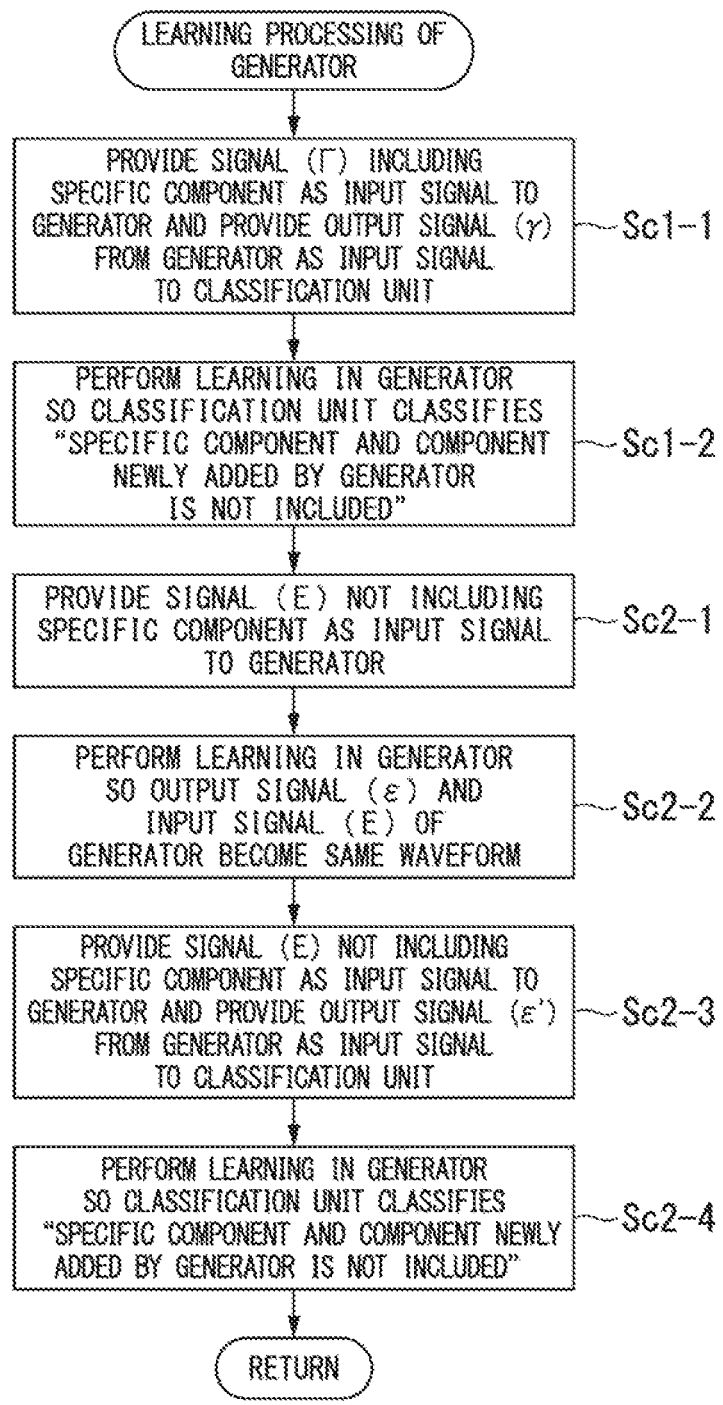
FIG. 6 is a flowchart showing the flow of learning processing by a generator according to the same embodiment.

FIG. 6 is a flowchart showing the flow of the learning processing of the generator 32 in step Sa2-2. The learning processing unit 35 provides a training-use multivariate signal (Γ) including the specific component to the generator 32 as an input signal. The generator 32 generates an output signal (γ) based on the internal weight coefficient and the input signal (Γ). The classification unit 31 takes the output signal (γ) output by the generator 32 as an input signal, calculates an output value based on the internal weight coefficient and the input signal (γ), and outputs a classification γ as the classification result as an input signal to the classification unit 31 (step Sc1-1).

The learning processing unit 35, based on the information indicated by the classification γ, causes the generator 32 to perform learning such that the information indicated by the classification γ becomes information that indicates that "the specific component and a component newly added by the generator 32 is not included" (step Sc1-2). That is to say, the learning processing unit 35 calculates the internal weight coefficient of the generator 32 so that the value of the classification γ approaches "0", and rewrites and updates the internal weight coefficient of the generator 32 with the calculated weight coefficient. The learning processing unit 35 writes and stores the calculated weight coefficient of the generator 32 in the storage unit 36.

The learning processing unit 35 provides a training-use multivariate signal (E) not including the specific component to the generator 32 as an input signal (step Sc2-1). The generator 32 generates an output signal (ε) based on the internal weight coefficient and the input signal (E). The learning processing unit 35 causes the generator 32 to perform learning such that the waveform of the input signal (E) and the waveform of the output signal (ε) become the same waveform (step Sc2-2).

That is to say, the learning processing unit 35 calculates the internal weight coefficient of the generator 32 based on the input signal (E) and the output signal (ε), such that the waveform of the input signal (E) and the waveform of the output signal (ε) become the same waveform. The learning processing unit 35 rewrites and updates the internal weight coefficient of the generator 32 with the calculated weight coefficient. The learning processing unit 35 writes and stores the calculated weight coefficient of the generator 32 in the storage unit 36.

After the weight of the generator 32 is updated in step Sc2-2, the classification unit 31 takes as an input signal the output signal (ε'), which is output by the generator 32 based on an input of the input signal (E) (step Sc2-3). The classification unit 31 calculates an output value based on the internal weight coefficient and the input signal (ε'), and outputs a classification ε' as the classification result.

The learning processing unit 35, based on the information indicated by the classification ε', causes the generator 32 to perform learning such that the information indicated by the classification ε' becomes information that indicates that "the specific component and a component newly added by the generator 32 is not included" (step Sc2-4). That is to say, the learning processing unit 35 calculates the internal weight coefficient of the generator 32 so that the value of the classification ε' approaches "0", and rewrites and updates the internal weight coefficient of the generator 32 with the calculated weight coefficient. The learning processing unit 35 writes and stores the calculated weight coefficient of the generator 32 in the storage unit 36.

In the learning processing of the classification unit 32 shown in FIG. 6, step Sc1-2 and step Sc2-4 represents supervised learning, which has information indicating "the specific component or a component newly added by the generator 32 is not included" as teaching data. Furthermore, step Sc2-2 represents supervised learning, which has the input signal (E) as teaching data.

Figure 7:
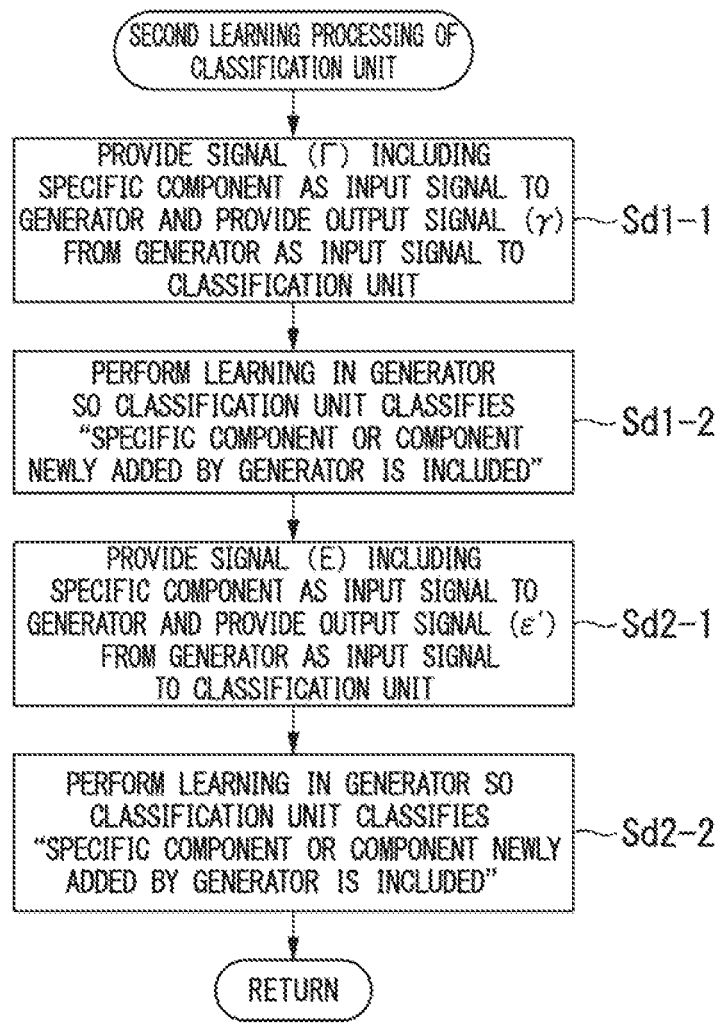
FIG. 7 is a flowchart showing the flow of second learning processing by the classification unit according to the same embodiment.

FIG. 7 is a flowchart showing the flow of the second learning processing of the classification unit 31 in step Sa2-3. For convenience of description, the flowchart of the learning processing of the generator 32 and the flowchart of the second learning processing of the classification unit 31 are shown separately. However, step Sd1-1 below represents the processing of step Sc1-1 in FIG. 6, and the processing of step Sd2-1 represents the processing of step Sc2-3 in FIG. 6. The processing of step Sd1-2 is performed using the processing result of step Sc1-1, and the processing of step Sd2-2 is performed using the processing result of step Sc2-3.

The learning processing unit 35, as a result of providing the training-use multivariate signal (Γ) including the specific component as an input signal to the generator 32, outputs the classification γ as the classification result from the classification unit 31 (step Sd1-1).

The learning processing unit 35, based on the information indicated by the classification γ, and in contrast to the learning performed with respect to the generator 32, causes the classification unit 31 to perform learning such that the information indicated by the classification γ becomes information representing that "the specific component or a component newly added by the generator 32 is included" (step Sd1-2). That is to say, the learning processing unit 35 calculates the internal weight coefficient of the classification unit 31 so that the value of the classification γ approaches "1", and rewrites and updates the internal weight coefficient of the classification unit 31 with the calculated weight coefficient. The learning processing unit 35 writes and stores the calculated weight coefficient of the classification unit 31 in the storage unit 36.

The learning processing unit 35, as a result of providing the training-use multivariate signal (E) not including the specific component as an input signal to the generator 32, outputs the classification ε' as the classification result from the classification unit 31 (step Sd2-1).

The learning processing unit 35, based on the information indicated by the classification ε', and in contrast to the learning performed with respect to the generator 32, causes the classification unit 31 to perform learning such that the information indicated by the classification ε' becomes information representing that "the specific component or a component newly added by the generator 32 is included" (step Sd2-2). That is to say, the learning processing unit 35 calculates the internal weight coefficient of the classification unit 31 so that the value of the classification ε' approaches "1", and rewrites and updates the internal weight coefficient of the classification unit 31 with the calculated weight coefficient. The learning processing unit 35 writes and stores the calculated weight coefficient of the classification unit 31 in the storage unit 36.

Returning to FIG. 2, information relating to the learned weight coefficient of the generator 32, which is stored in the storage unit 36 at the time learning processing by the model formulation unit 3 in step Sa2 is completed, becomes signal separation model data which is capable of separating the specific component.

The test signal acquisition unit 4 takes an externally provided, arbitrary testing-use multivariate signal, in which it is not known whether the signal includes the specific component (step Sa3). The signal separation removal unit 5 reads the learned weight coefficient of the generator 32 stored in the storage unit 36 of the model formulation unit 3, that is to say, the signal separation model data, and internally generates a generator 32a based on the read signal separation model data.

The signal separation removal unit 5 provides the testing-use multivariate signal acquired by the test signal acquisition unit 4 to the internally generated generator 32a as an input signal. The generator 32a generates and outputs a signal having a waveform in which the specific component has been separated and removed from the waveform of the input signal. The signal separation removal unit 5 outputs the output signal of the generator 32a to the outside. If learning in the model formulation unit 3 is sufficiently performed, the output signal of the signal separation removal unit 5 becomes a signal as follows. That is to say, if the specific component is not included in the testing-use multivariate signal, the signal becomes the same as the testing-use multivariate signal. On the other hand, if the specific component is included in the testing-use multivariate signal, the signal becomes a signal in which the specific component has been separated and removed from the testing-use multivariate signal.

Figure 8:
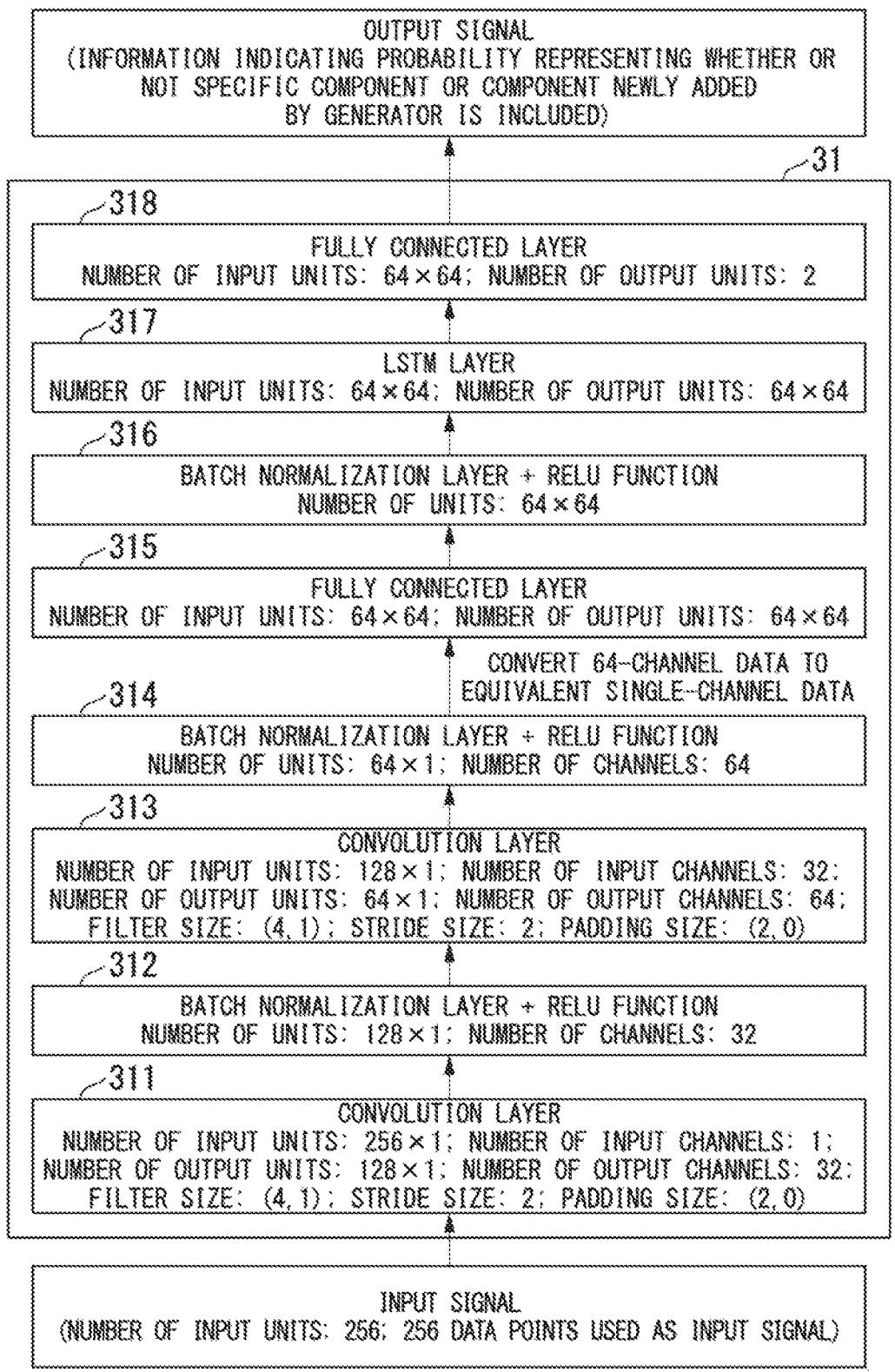
FIG. 8 is a diagram showing an example of a specific configuration of the classification unit according to the same embodiment.
Figure 9:
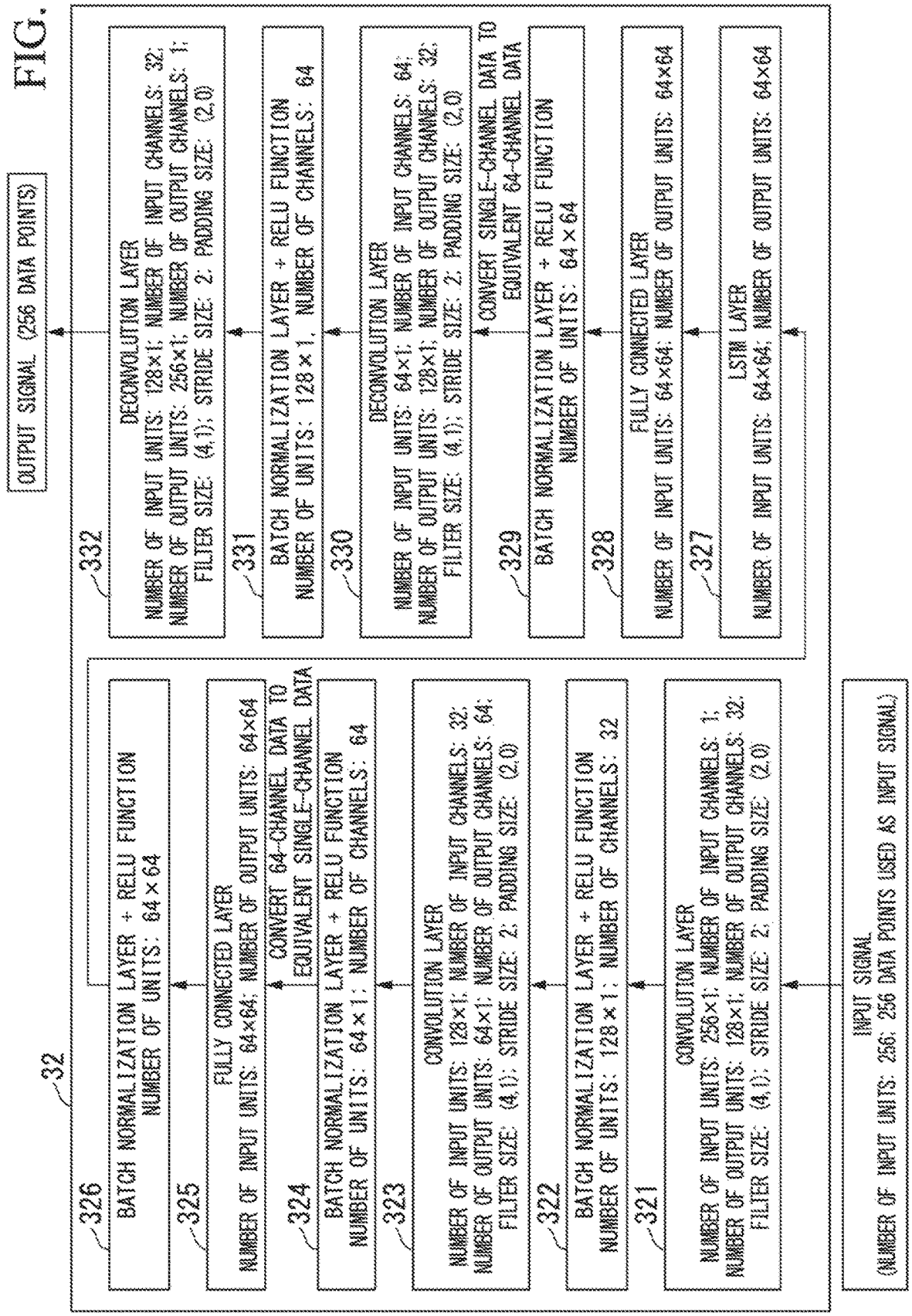
FIG. 9 is a diagram showing an example of a specific configuration of the generator according to the same embodiment.

FIG. 8 and FIG. 9 are diagrams respectively showing an example of a specific configuration of the classification unit 31 and the generator 32. As shown in FIG. 8, the classification unit 31 has a multilayer configuration in which, in order from the input side, a "convolution layer" 311, a "batch normalization layer+relu (Rectified Liner Unit) function" 312, a "convolution layer" 313, a "batch normalization layer+relu function" 314, a fully connected layer 315, a "batch normalization layer+relu function" 316, an LSTM (Long short-term memory) layer 317, and a fully connected layer 318 are connected.

As shown in FIG. 9, the generator 32 has a multilayer configuration in which, in order from the input side, a "convolution layer" 321, a "batch normalization layer+relu function" 322, a "convolution layer" 323, a "batch normalization layer+relu function" 324, a fully connected layer 325, a "batch normalization layer+relu function" 326, an LSTM (Long short-term memory) layer 327, a fully connected layer 328, a "batch normalization layer+relu function" 329, a deconvolution layer 330, a "batch normalization+relu function" 331, and a deconvolution layer 332 are connected.

The input signal of the classification unit 31 is a signal in which 256 points are selected from among the most recent points in a consecutive time series signal, or a signal of 256 points output by the generator 32. The values of the 256 points are each taken by 256 input units of the convolution layer 311. The output signals of the classification unit 31 are values output from two output units. From the two output values, for example, a probability value between 0 and 1 is calculated, where information indicating "the specific component or a component newly added by the generator 32 is included" is represented by "1", and information indicating "the specific component and a component newly added by the generator 32 is not included" is represented by "0" as mentioned above.

The input signal of the generator 32 is a signal in which 256 points are selected from among the most recent points in a consecutive time series signal, and the values of each of the 256 points are taken by 256 input units of the convolution layer 321. The output signal of the generator 32 becomes the same 256 points as the input signal.

Hereunder, the configuration of each layer will be described. In the description below, a unit represents the number of data in a predetermined minimum unit data length (256 points in the example of FIG. 8 and FIG. 9) selected from a processing target signal. Furthermore, a channel (ch) represents the number of units when a plurality of units consecutively exists.

In FIG. 8 and FIG. 9, the "convolution layers" 311, 313, 321, and 323 perform a convolution operation based on a predetermined number of filters by applying a blank space (hereunder referred to as a padding) of a predetermined size at an interval (hereunder referred to as a stride) at which a predetermined filter is applied to the input signal.

The configuration of the "convolution layers" 311 and 321 is as follows: number of input units: 256×1; number of input channels: 1; number of output units: 128×1; number of output channels: 32; filter size: (4,1); stride size: 2; and padding size: (2,0). As a result, a convolution operation is performed by applying 32 types of 4×1 filters to a single-channel input signal constituted by 256×1 units after adding a 2×0 blank space at every two-point interval, and a 32-channel output signal configured by 128×1 units is then output.

The configuration of the "convolution layers" 313 and 323 is as follows: number of input units: 128×1; number of input channels: 32; number of output units: 64×1; number of output channels: 64; filter size: (4,1); stride size: 2; and padding size: (2,0). As a result, a convolution operation is performed by applying 64 types of 4×1 filters to a 32-channel input signal constituted by 128×1 units after adding a 2×0 blank space at every two-point interval, and a 64-channel output signal configured by 64×1 units is then output.

The "deconvolution layers" 330 and 332 perform a deconvolution operation based on a predetermined number of filters by applying a padding of a predetermined size at a predetermined stride to the input signal.

The configuration of the "deconvolution layer" 330 is as follows: number of input units: 64×1; number of input channels: 64; number of output units: 128×1; number of output channels: 32; filter size: (4,1); stride size: 2; and padding size: (2,0). As a result, a deconvolution operation is performed by applying 32 types of 4×1 filters to a 64-channel input signal constituted by 64×1 units after adding a 2×0 blank space at every two-point interval, and a 32-channel output signal configured by 128×1 units is then output.

The configuration of the "deconvolution layer" 332 is as follows: number of input units: 128×1; number of input channels: 32; number of output units: 256×1; number of output channels: 1; filter size: (4,1); stride size: 2; and padding size: (2,0). As a result, a deconvolution operation is performed by applying a single type of 4×1 filter to a 32-channel input signal constituted by 128×1 units after adding a 2×0 blank space at every two-point interval, and a single-channel output signal configured by 256×1 units is then output.

In the "batch normalization layer+relu function" 312, 314, 316, 322, 324, 326, 329, and 331, the batch normalization layer reduces the bias in the distribution of an input signal by performing normalization using an average value and a variance value of the input signal. The relu function is an activation function that produces a non-linear output with respect to an input. In the batch normalization layer, a single unit has an input and an output, and the relu function is applied with respect to the output.

The configuration of the "batch normalization layer+relu function" 312 and 322 is as follows: number of units: 128×1; and number of channels: 32. The configuration of the "batch normalization layer+relu function" 314 and 324 is as follows: number of units: 64×1; and number of channels: 64. In the "batch normalization layer+relu function" 316, 326, and 329, the number of units is 64×64. The configuration of the "batch normalization layer+relu function" 331 is as follows: number of units: 128×1; and number of channels: 64.

The LSTM layers 317 and 327 have a layer including an internal memory and gate, and maintain a long-term dependency between the training-use information provided in the learning process by using the memory for long-term storage. The configuration of the LSTM layers 317 and 327 is as follows: number of input units: 64×64; and number of output units: 64×64.

In the fully connected layers 315, 318, 325, and 328, all of the input nodes and output nodes are connected between an input layer and an output layer, and an output signal of an important input node is reflected in the following output node by applying an appropriate weight coefficient. The configuration of the fully connected layers 315, 325, and 328 is as follows: number of input units: 64×64, and number of output units: 64×64. Further, the 4,096 input units are each connected to the 4,096 output units. The configuration of the fully connected layer 318 is as follows: number of input units: 64×64, and number of output units: 2. Further, the 4,096 input units are each connected to the two output units.

The fully connected layers 315, 318, 325, and 328, and the LSTM layers 317 and 327 are configured to target a single channel. Consequently, between the "batch normalization layer+relu function" 314 and the fully connected layer 315 in the classification unit 31, and between the "batch normalization layer+relu function" 324 and the fully connected layer 325 in the generator 32, the 64-channel configuration is converted to a single-channel configuration. Furthermore, between the "batch normalization layer+relu function" 329 and the deconvolution layer 330 in the generator 32, the single-channel configuration is converted to a 64-channel configuration.

Conversion of a 64-channel configuration to a single-channel configuration refers to arranging the values of 64 units and 64 channels side-by-side to form 4,096 single-channel signals. In contrast, conversion of a single-channel configuration to a 64-channel configuration refers to, for example, forming 64 channels of a 64-unit signal when 4,096 single-channel signals exist.

In the classification unit 31, the convolution layers 311 and 313, and the "batch normalization layer+relu function" 312 and 314, are repeatedly applied to extract a time-varying pattern in stages. Then, the fully connected layer 315, the "batch normalization layer+relu function" 316, the LSTM layer 317, and the fully connected layer 318 perform feature extraction and classification including the long-term dependence.

In the generator 32, similarly to the classification unit 31, the convolution layers 321 and 323, the "batch normalization layer+relu function" 322, 324, 326 and 329, the LSTM layer 327, and the fully connected layers 325 and 328 extract a time-varying pattern including the long-term dependence. Then, the deconvolution layers 330 and 332, and the "batch normalization layer+relu function" 331 generate a pseudo-signal.

The learning processing corresponding to steps Sc2-1 and Sc2-2 in FIG. 6 applies an error function such as a Euclidean distance at the time the generator 32 performs learning, that is to say, causes the waveform of the input signal of the signal (E) not including the specific component to become the same waveform as the waveform of the output signal (ε) output by the generator 32. The error function in the learning processing is not limited to a Euclidean distance. A distance function representing shape similarity, such as an L1 distance, may also be applied.

The learning processing unit 35 applies an error function such as the cross-entropy of a softmax function, at the time learning is performed such that the classification unit 31 is capable of accurately classifying whether or not an input signal includes the specific component. The error function in the learning processing is not limited to the cross-entropy of a softmax function. The error function in the learning processing may also apply an Earth Mover's Distance in the same manner as a Wasserstein GAN, an energy function in the same manner as an energy-based GAN, or an L2 distance in the same manner as a least squares GAN.

An error weight ratio of the classification unit 31 and the generator 32 is, for example, determined as follows. The error when a Euclidian distance is applied as an error function at the time learning is performed by the generator 32 such that the input signal (E) and the output signal (ε) become the same waveform is referred to as a first error. The cross-entropy error of a softmax function applied as an error function at the time the classification unit 31 classifies and outputs the classification γ and the classification ε' is referred to as a second error. At this time, for example, a ratio of "1:0.001" is applied as the error weight ratio of the first error and the second error. The error weight ratio is not limited to this ratio, and may be another ratio.

After calculating the error using an error function, the learning processing unit 35 performs optimization by rewriting and updating the weight coefficients of the layers 311 to 318 of the classification unit 31, and the layers 321 to 332 of the generator 32 with weight coefficients calculated by an error back-propagation method. Adam (adaptive moment estimation) is applied as the optimization method. The optimization method is not limited to Adam, and another optimization method such as a stochastic gradient method may be applied.

(Simulation Results)

Figure 10:
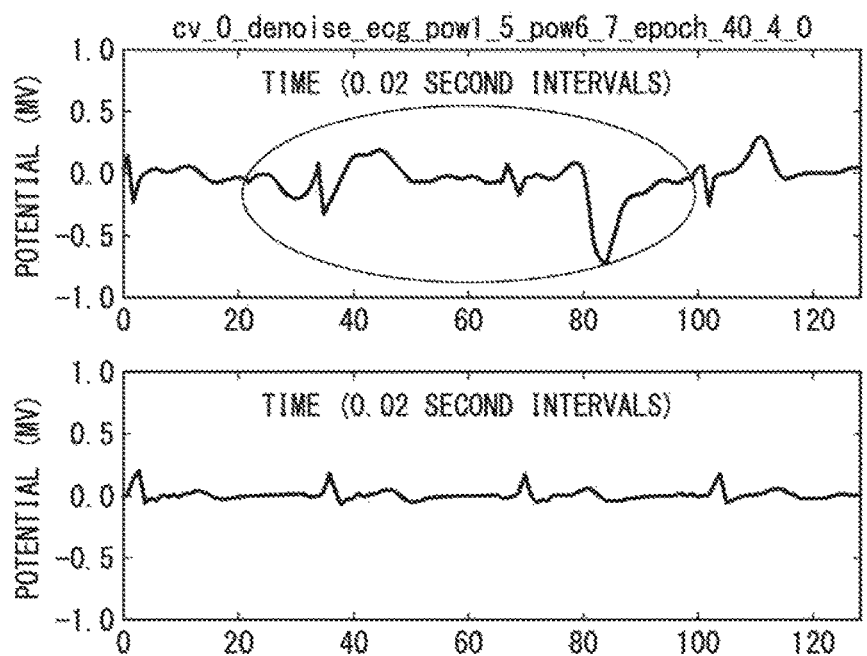
FIG. 10 is a simulation result (1) using the learning-type signal separation device according to the same embodiment.
Figure 11:
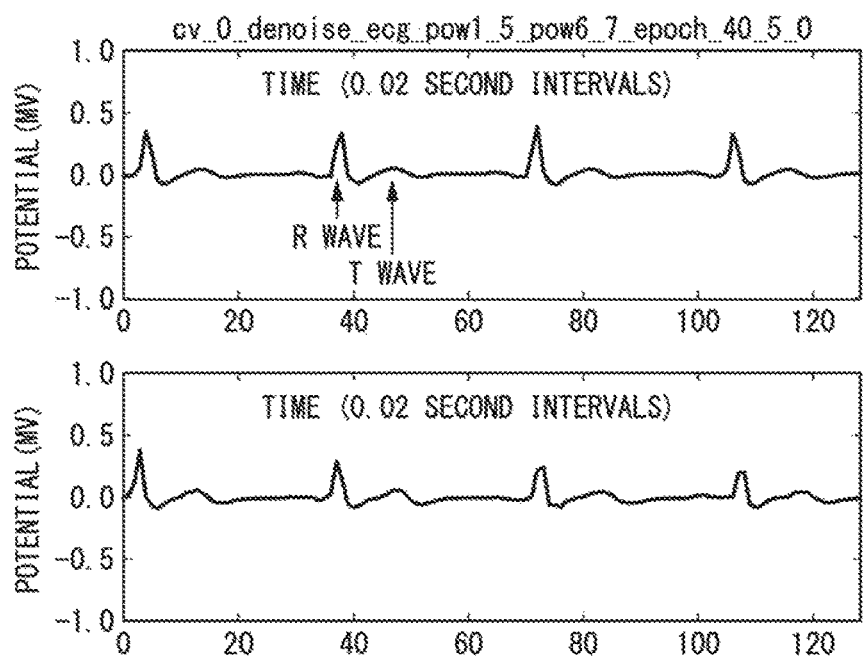
FIG. 11 is a simulation result (2) using the learning-type signal separation device according to the same embodiment.

FIG. 10 and FIG. 11 are diagrams showing simulation results when signal separation model data is applied to the signal separation removal unit 5, and an electrocardiogram signal is provided as a testing-use multivariate signal. The upper graph in FIG. 10 is a signal representing an example of a multivariate signal (Γ) including the specific component, and the lower graph is an output signal of the signal. The upper graph in FIG. 11 is a signal representing an example of a multivariate signal (E) not including the specific component, and the lower graph is an output signal of the signal. In each graph, the vertical axis is the potential (mV), and the horizontal axis is time. The data interval included in the signal is every 0.02 seconds.

A typical electrocardiogram, for example, as shown in the upper graph in FIG. 11, displays a model which is repeated at fixed intervals, wherein the occurrence of an R wave, which appears as a peak, is followed by the generation of a T wave, which is a slightly higher wave. Referring to the black circled area in the upper graph of FIG. 10, it can be understood that a change has occurred in the potential which is larger than that of the R wave. Furthermore, it can be understood that an R wave pattern is included within the signal distortion or noise. Referring to the output signal ($\gamma$) in the lower graph of FIG. 10, which is the output of the signal separation removal unit 5, it can be understood that the signal distortion or noise is reduced, and that the R wave pattern is reproduced at substantially the same time as the position of the R wave of the input signal ($\Gamma$). Furthermore, it can additionally be understood that the T wave is reproduced.

Next, referring to FIG. 11, as shown in the upper graph in FIG. 11, it can be understood that the R wave and the T wave are clearly measured in the case of the input signal (E) not including the specific component. Referring to the output signal ($\varepsilon$) in the lower graph, which is the output of the signal separation removal unit 5, it can be understood that a substantially unchanged signal, that is to say, the R wave and the T wave are reproduced at substantially the same time as in the input signal (E). In the graphs in FIG. 11, the potential of the R wave peak is slightly different between the input signal (E) and the output signal ($\varepsilon$). This difference in R wave peak potential can be reduced by making the error smaller by increasing the number of training-use multivariate signals and causing the generator 32 to perform learning such that the waveform of the input signal (E) becomes substantially the same waveform as the waveform of the output signal ($\varepsilon$).

As a result of the configuration of the above embodiment, in the learning-type signal separation device 1, the training signal acquisition unit 2 acquires and classifies a signal as a training-use multivariate signal including the specific component or a training-use multivariate signal not including the specific component. The model formulation unit 3, based on a training-use multivariate signal including the specific component and a training-use multivariate signal not including the specific component, performs learning that generates a data series signal in which the specific component has been separated and removed from the data series of the training-use multivariate signal acquired by the training signal acquisition unit 2, and generates learned data. The test signal acquisition unit 4 acquires an arbitrary multivariate signal, in which it is not known whether the signal includes the specific component. The signal separation removal unit 5, based on the arbitrary multivariate signal acquired by the test signal acquisition unit 4 and the learned data generated by the model formulation unit 3, generates a data series signal in which the specific component has been separated and removed from the data series of the arbitrary multivariate signal.

Therefore, the model formulation unit 3 learns the characteristics of the specific component to be separated using a training-use multivariate signal which is prelabeled as to whether or not the specific component is included, and the signal separation removal unit 5 uses the learned data to separate and remove the specific component from the arbitrary multivariate signal.

As a result, even if it the frequency characteristics of the specific component are not known, it is possible to perform processing such as an analysis after removing the specific component from a multivariate signal measured at a single point. Furthermore, it is unnecessary to construct a model for each component of a multivariate signal in advance.

In other words, even if a model for each signal component of a multivariate signal is not constructed in advance, and further, even if the frequency characteristics of the specific component to be classified are not obtained in advance, it is possible to separate and remove the specific component from a multivariate signal measured at a single point.

Therefore, for a signal measured at a single point and a signal in which modeling of the signal components is difficult, it becomes possible to separate and remove a specific component included in the signal, even when the characteristics of a specific component such as signal distortion or noise is unknown. For example, unnecessary components such as signal distortion or noise can be separated and removed from a signal such as a biological signal in which various factors act in combination.

A case where the signal is a biological signal is exemplified in the above embodiment. However, the same applies to a case where the signal is a signal such as a sound or an image. Modeling of the signal components is difficult in some signals such as a sound or an image. Even with such signals, it is possible to separate and remove a specific component with unknown characteristics from a signal such as a sound or an image.

Furthermore, in the embodiment above, by repeating the learning processing in FIG. 5 to FIG. 7, as a result of the first learning processing of the classification unit 31, the classification unit 31 outputs a classification result indicating that "the specific component or a component newly added by the generator 32 is included" when a training-use multivariate signal including the specific component is provided as an input signal. Moreover, the classification unit 31 outputs a classification result indicating that "the specific component and a component newly added by the generator 32 is not included" when a training-use multivariate signal not including the specific component is provided as an input signal.

Furthermore, as a result of the second learning processing of the classification unit 31 and the learning processing of the generator 32, the classification unit 31 outputs a classification result indicating that "the specific component or a component newly added by the generator 32 is included", which is a classification result output by the classification unit 31 which takes the output signal of the generator 32 as an input signal, irrespective of whether or not the specific component is included in the input signal provided to the generator 32. On the other hand, the generator 32 outputs an output signal such that the classification result output by the classification unit 31, which takes the output signal of the generator 32 as an input signal, becomes a classification result indicating that "the specific component or a component newly added by the generator 32 is not included" irrespective of whether or not the specific component is included in the input signal.

In such a manner, based on a learning method by a GAN, the classification unit 31 performs learning such that accurate classification is performed. On the other hand, the generator 32 performs learning such that it generates a signal that becomes incorrectly classified by the classification unit 31 as a signal in which "the specific component and a component newly added by the generator 32 is not included". Therefore, the classification unit 31 and the generator 32 perform learning as if they are in competition with each other. As a result, the classification unit 31 can perform classification with a higher accuracy by performing the second learning processing using the multivariate signals generated by the generator 32 rather than performing the first learning processing alone. Furthermore, the generator 32 generates a data series in which the specific component has been separated and removed from the data series of the input signal with the same high accuracy.

Consequently, after sufficient learning has been performed, when the input signal is a multivariate signal not including the specific component, the generator 32 outputs the input signal as is. Moreover, after sufficient learning has been performed, when the input signal is a multivariate signal including the specific component, the generator 32 generates and outputs a data series signal not including the specific component, that is to say, a data series signal in which the specific component has been separated and removed from the data series of the input signal. In addition, after sufficient learning has been performed, the generator 32 itself no longer adds a new component.

As a result of applying a GAN, if almost all of the measurement target signals include a common characteristic despite being difficult to model, such as a biological signal of a cardiac potential, the model formulation unit 3 performs learning with respect to the characteristics of the specific component such as signal distortion or noise, and the common characteristic. Consequently, rather than directly removing the specific component such as signal distortion or noise from the measured signal, it is possible to generate a data series signal that does not include the specific component and includes the common characteristic, based on a measured signal data series. Therefore, by applying the signal separation model data generated by the model formulation unit 3, it is possible to generate a data series signal in which the specific component has been separated and removed from the signal data series as long as the measured arbitrary signal includes the common characteristic.

Furthermore, in the above embodiment, the learning processing of the generator 32 is performed in step Sc2-1 and Sc2-2 in FIG. 6. Consequently, the generator 32 outputs the same data series (waveform) signal as the data series (waveform) of the input signal when a training-use multivariate signal (E) not including the specific component is provided as the input signal. As a result, in addition to the learning method by the GAN, the generator 32 is capable of separating and removing the specific component more accurately.

Furthermore, in the above embodiment, the learning processing unit 35 causes the classification unit 31 learn that "the specific component or a component newly added by the generator 32 is included" or "the specific component and a component newly added by the generator 32 is not included". However, the present invention is not limited to the present embodiment. For example, the learning processing unit 35 may cause the classification unit 31 to only learn that "the specific component is included" or "the specific component is not included".

However, in the case of only learning that the "specific component is included" or that "the specific component is not included" it is necessary for the processing of steps Sc2-3 and Sc2-4 in the learning processing of the generator 32 shown in FIG. 6, and for the processing of steps Sd2-1 and Sd2-2 in the second learning processing of the classification unit 31 shown in FIG. 7 to not be performed. The reason for this is because, as a result of performing sufficient learning, the generator 32 generates and outputs an output signal ($\varepsilon$) having the same waveform when a multivariate signal (E) not including the specific component is provided, and the waveforms of the output signal ($\varepsilon$) and the input signal (E) are not similar when sufficient learning has not been performed. Consequently, in the process of learning, if the classification unit 31 or the generator 32 performs learning based on the output signal ($\varepsilon$), there is a concern that learning may be performed in an incorrect direction.

In the embodiment above, the reason for making "a component newly added by the generator 32" a separation target in addition to "the specific component" is as follows. If the diversity in the multivariate signal (E) not including the specific component is small, that is to say, if the number of examples of the multivariate signal (E) is too small, there is a possibility that the learning processing unit 35 may cause the generator 32 to overlearn such that one of the multivariate signals (E) is output if a multivariate signal ($\Gamma$) including the specific component is provided as an input signal.

In contrast, by making "a component newly added by the generator 32" a separation target, it can be made a suitable classification target of the classification unit 31. Consequently, because the processing of steps Sc2-3 and Sc2-4 in the learning processing of the generator 32 shown in FIG. 6, and the processing of steps Sd2-1 and Sd2-2 in the second learning processing of the classification unit 31 shown in FIG. 7 can be added, overlearning as described above can be avoided. That is to say, by making "a component newly added by the generator 32" a separation target, learning can be performed such that a component newly added by the generator 32 is separated in addition to the specific component, and the specific component can be separated more accurately.

Furthermore, in the embodiment above, even in a case where the learning processing unit 35 has caused the classification unit 31 and the generator 32 to perform sufficient learning, the output signal generated by the generator 32 based on the input signal depends on the training-use multivariate signals that are provided. Consequently, if a multivariate signal not including the specific component is provided as an input signal of the learned generator 32, the generator 32 generates an output signal having substantially the same waveform as the waveform of the input signal. However, it does not necessarily always generate and output a signal having exactly the same waveform as the input signal.

Furthermore, in the above embodiment, the number of times the loop processing of L1s to L1e in FIG. 3 is performed is a predetermined frequency. However, the processing may be repeated until an output value of the classification unit 31 or the generator 32 satisfies a predetermined condition such as a threshold.

Moreover, in the above embodiment, the order of the processing shown in FIG. 3 is; step Sa2-1 of the first learning processing of the classification unit, step Sa2-2 of the learning processing of the generator 32, and step Sa2-3 of the second learning processing of the classification unit. However, the order of the learning processing may be interchanged.

In addition, in the above embodiment, a multivariate signal composed of a plurality of additive components is targeted, but a univariate signal including common features may be targeted.

In the above embodiment, a case is exemplified in which a multivariate signal or a univariate signal is the biological signal in an electrocardiogram. However, it is not limited to this example. The biological signal may be, for example, an electromyogram, an electroencephalogram, blood pressure, blood flow, body temperature, concentration of components in body fluid, and the like. Furthermore, the biological signal may be information relating to a body movement obtained by acceleration. The body movement is, for example, posture, motion, or gait. According to the above embodiment, unnecessary components such as signal distortion or noise can be separated and removed, even if the signal is one in which various factors act in combination, such as in a biological signal other than the electrocardiogram described above.

Furthermore, in the above embodiment, the signal separation removal unit 5 reads the signal separation model data from the storage unit 36, and internally generates the generator 32a, which has the same configuration as the generator 32. However, processing may be performed using the generator 32 of the model formulation unit 3 that separates and removes a specific component from the testing-use multivariate signal acquired by the test signal acquisition unit 4.

The learning-type signal separation device 1 of the embodiment described above may be realized by a computer. In this case, a program for realizing the functions may be recorded in a computer-readable recording medium, and the functions may be realized by a computer system reading and executing the program recorded on the recording medium. The "computer system" referred to here is assumed to include an OS and hardware such as a peripheral device. Furthermore, the "computer-readable recording medium" refers to a portable medium such as a flexible disk, a magnetic optical disk, a ROM, or a CD-ROM, or a storage device such as a hard disk built into a computer system. In addition, the "computer-readable recording medium" may include those that dynamically retain the program for a short time, such as a communication line that transmits the program via a network such as the Internet or a communication line such as a telephone line, and those that retain the program for a fixed time, such as the volatile memory inside a computer system serving as a server or a client in this case. Furthermore, the program may be one capable of realizing some of the functions described above. Further, the functions described above may be realized in combination with a program already recorded in the computer system, and may be realized by using a programmable logic device such as an FPGA (Field Programmable Gate Array).

The embodiments of the present invention were described in detail above with reference to the drawings. However, specific configurations are in no way limited to the embodiments, and include designs and the like within a scope not departing from the spirit of the present invention.

INDUSTRIAL APPLICABILITY

The present invention enables, for a signal measured at a single point and a signal in which modeling of the signal components is difficult, the separation and removal of a specific component included in the signal, even when the characteristics of a specific component such as the signal distortion or noise is unknown.

REFERENCE SYMBOLS

1 Learning-type signal separation device
2 Training signal acquisition unit
3 Model formulation unit
4 Test signal acquisition unit
5 Signal separation removal unit
31 Classification unit
32 Generator
35 Learning processing unit
36 Storage unit

The invention claimed is:

1. A learning-type signal separation method performed using a model formulation unit, which performs learning processing based on a training-use signal including a specific component, and a training-use signal not including the specific component, the training-use signals including a common characteristic,
   wherein the learning-type signal separation method includes:
   classifying and acquiring the training-use signal including the specific component and the training-use signal not including the specific component;
   generating learned data by causing the model formulation unit to perform learning processing based on the training-use signals and information indicating whether or not the specific component is included in the training-use signal, to generate a data series signal in which the specific component has been separated and removed from a data series of the training-use signal;
   acquiring any signal including the common characteristic; and
   generating, based on the acquired any signal and the generated learned data, a data series signal in which the specific component has been separated and removed from a data series of the any signal,
   wherein the model formulation unit is a GAN (Generative Adversarial Network) including a classification unit, a generator, and a learning processing unit that causes the classification unit and the generator to perform learning,
   the learning-type signal separation method further comprises:
   providing, by the learning processing unit, taking the training-use signal as an input signal, the input signal and information indicating whether or not the specific component is included in the input signal to the classification unit and the generator; and
   causing the classification unit to perform learning such that the specific component is included in the input signal, while causing the generator to perform learning so as to cause the classification unit to classify that the specific component is not included in the input signal, at the time an output signal of the generator is provided as the input signal of the classification unit;
   in the generating, based on signal separation model data and the acquired any signal that is measured at a single point, the data series signal in which the specific component indicating a frequency characteristic has been separated and removed from the data series of the any signal are generated, the signal separation model data being learned data from the generator among the generated learned data,
   wherein the learning-type signal separation method further comprises:
   while causing the generator to perform learning such that the classification unit outputs a classification result indicating that the the specific component and a component newly added by the generator are not included in the input signal at the time the output signal output by the generator resulting from providing the input signal including the specific component to the generator is provided to the classification unit as the input signal,
   causing the classification unit to perform learning such that the classification unit outputs the classification result indicating that the specific component or the component newly added is included in the input signal at the time the output signal output by the generator after the learning resulting from providing the input signal including the specific component to the generator after the learning is provided to the classification unit as the input signal; and while causing the generator to perform learning such that the same data series signal as the data series of the input signal is generated when the specific component is not included in the input signal provided to the generator and to perform learning such that the classification unit outputs the classification result indicating that the specific component and the component newly added are not included in the input signal at the time the output signal output by the generator resulting from providing the input signal not including the specific component to the generator is provided to the classification unit as the input signal, causing the classification unit to perform learning such that the classification unit outputs the classification result indicating that the specific component or the component newly added is included in the input signal at the time the output signal output by the generator after the learning resulting from providing the input signal not including the specific component to the generator after the learning is provided to the classification unit as the input signal, and the component newly added indicates a difference component between the output signal output by the generator resulting from providing the input signal to the generator, and the input signal.

2. The learning-type signal separation method according to claim 1 wherein processes by the learning processing unit further comprises:

causing the classification unit to perform learning such that the classification unit outputs a classification result indicating that the specific component is included when the specific component is included in the input signal, and outputs a classification result indicating that the specific component is not included in the input signal when the specific component is not included in the input signal;

causing the classification unit to perform learning such that the classification unit outputs a classification result indicating that the specific component is included in the input signal at the time an output signal output by the generator resulting from providing the input signal including the specific component to the generator is provided to the classification unit as the input signal; and causing the generator to perform learning such that the classification unit outputs a classification result indicating that the specific component is not included in the input signal at the time an output signal output by the generator resulting from providing the input signal including the specific component to the generator is provided to the classification unit as the input signal.

3. The learning-type signal separation method according to claim 1, wherein the training-use signal, the any signal, and the data series signal are multivariate signals constituted by a plurality of additive components, or a univariate signal.

4. The learning-type signal separation method according to claim 1, wherein the training-use signal, the any signal, and the data series signal are measured biological signals, and the specific component is an unnecessary component added to a biological signal.

5. The learning-type signal separation method according to claim 1 wherein the data series is a waveform or a frequency.

6. A learning-type signal separation device including:
at least one memory configured to store instructions; and
at least one processor configured to execute the instruction to:

acquire and classifies a signal as a training-use signal including a specific component or a training-use signal not including the specific component, the training-use signals including a common characteristic;

perform, based on the training-use signal acquired by a training signal acquisition unit and information indicating whether or not the specific component is included in the training-use signal, learning that generates a data series signal in which the specific component has been separated and removed from a data series of the training-use signal, and generate learned data;

acquire any signal including the common characteristic; and generate, based on the any signal acquired by a test signal acquisition unit and the generated learned data, a data series signal in which the specific component has been separated and removed from a data series of the any signal, wherein the at least one processor is configured to execute the instructions to constitute a GAN (Generative Adversarial Network) including a classification unit, a generator, and a learning processing unit that causes the classification unit and the generator to perform learning, the learning processing unit is configured to:
provide taking the training-use signal as an input signal, the input signal and information indicating whether or not the specific component is included in the input signal to the classification unit and the generator;

cause the classification unit to perform learning such that the specific component is included in the input signal, while causing the generator to perform learning so as to cause the classification unit to classify that the specific component is not included in the input signal, at the time an output signal of the generator is provided as the input signal of the classification unit;

wherein, based on signal separation model data and the acquired any signal that is measured at a single point, the data series signal in which the specific component indicating a frequency characteristic has been separated and removed from the data series of the any signal are generated, the signal separation model data being learned data from the generator among the generated learned data, wherein the learning processing unit is further configured to:

while cause the generator to perform learning such that the classification unit outputs a classification result indicating that the the specific component and a component newly added by the generator are not included in the input signal at the time the output signal output by the generator resulting from providing the input signal including the specific component to the generator is provided to the classification unit as the input signal, cause the classification unit to perform learning such that the classification unit outputs the classification result indicating that the specific component or the component newly added is included in the input signal at the time the output signal output by the generator after the learning resulting from providing the input signal including the specific component to the generator after the learning is provided to the classification unit as the input signal; and while cause the generator to perform learning such that the same data series signal as the data series of the input signal is generated when the specific component is not included in the input signal provided to the generator and to perform learning such that the classification unit outputs the classification result indicating that the specific component and the component newly added are not included in the input signal at the time the output signal output by the generator resulting from providing the input signal not including the specific component to the generator is provided to the classification unit as the input signal, cause the classification unit to perform learning such that the classification unit outputs the classification result indicating that the specific component or the component newly added is included in the input signal at the time the output signal output by the generator after the learning resulting from providing the input signal not including the specific component to the generator after the learning is provided to the classification unit as the input signal, and the component newly added indicates a difference component between the output signal output by the generator resulting from providing the input signal to the generator, and the input signal.

* * * * *